US00PP19516P2

(12) United States Plant Patent
Bernuetz

(10) Patent No.: US PP19,516 P2
(45) Date of Patent: Dec. 2, 2008

(54) ***SCAEVOLA* PLANT NAMED 'BONSCALIB'**

(50) Latin Name: *Scaevola aemula*
Varietal Denomination: Bonscalib

(75) Inventor: Andrew Bernuetz, Silversdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 0 days.

(21) Appl. No.: 11/998,801

(22) Filed: Nov. 30, 2007

(51) Int. Cl.
*A01H 5/00* (2006.01)

(52) U.S. Cl. ..... Plt./363

(58) Field of Classification Search ..... Plt./363
See application file for complete search history.

*Primary Examiner*—Kent L. Bell
*Assistant Examiner*—Geogia Helmer
(74) *Attorney, Agent, or Firm*—C. A. Whealy

(57) ABSTRACT

A new and distinct cultivar of *Scaevola* plant named 'Bonscalib', characterized by its compact, mounded and semi-trailing plant habit; freely branching habit; early and freely flowering habit; long flowering period; light violet-colored flowers; and good garden performance.

1 Drawing Sheet

Botanical designation: *Scaevola aemula.*
Cultivar denomination: 'Bonscalib'.

BACKGROUND OF THE INVENTION

The present invention relates to a new and distinct cultivar of *Scaevola,* botanically known as *Scaevola aemula,* and hereinafter referred to by the name 'Bonscalib'.

The new *Scaevola* is a product of a planned breeding program conducted by the Inventor in Yellow Rock, New South Wales, Australia. The objective of the breeding program is to create new freely-flowering *Scaevola* cultivars with attractive flower coloration.

The new *Scaevola* originated from an open-pollination in Yellow Rock, New South Wales, Australia in March/April, 2003 of a proprietary selection of *Scaevola aemula* identified as code number 00-38.1, not patented, as the female, or seed, parent with an unknown proprietary selection of *Scaevola aemula,* as the male, or pollen, parent. The cultivar Bonscalib was discovered and selected by the Inventor as a flowering plant within the progeny of the stated open-pollination in a controlled environment in Yellow Rock, New South Wales, Australia.

Asexual reproduction of the new *Scaevola* by vegetative cuttings in a controlled environment in Yellow Rock, New South Wales, Australia since December, 2004, has shown that the unique features of this new *Scaevola* are stable and reproduced true to type in successive generations.

SUMMARY OF THE INVENTION

The cultivar Bonscalib has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Bonscalib'. These characteristics in combination distinguish 'Bonscalib' as a new and distinct cultivar of *Scaevola:*

1. Compact, mounded and semi-trailing plant habit.
2. Freely branching habit.
3. Early and freely flowering habit.
4. Long flowering period.
5. Light violet-colored flowers.
6. Good garden performance.

Plants of the new *Scaevola* can be compared to plants of the female parent selection. Plants of the new *Scaevola* differ from plants of the female parent selection in the following characteristics:

1. Plants of the new *Scaevola* are more compact and denser than plants of the female parent selection.
2. Plants of the new *Scaevola* flower earlier than plants of the female parent selection.

Plants of the new *Scaevola* can be compared to plants of the *Scaevola aemula* cultivar Cool Sapphire, not patented. In side-by-side comparisons conducted in Yellow Rock, New South Wales, Australia, plants of the new *Scaevola* differed from plants of the cultivar Cool Sapphire in the following characteristics:

1. Plants of the new *Scaevola* were more compact than plants of the cultivar Cool Sapphire.
2. Stems of plants of the new *Scaevola* were pubescent whereas stems of plants of the cultivar Cool Sapphire were glabrous.
3. Plants of the new *Scaevola* had shorter leaves than plants of the cultivar Cool Sapphire.
4. Plants of the new *Scaevola* had larger flowers than plants of the cultivar Cool Sapphire.

BRIEF DESCRIPTION OF THE PHOTOGRAPHS

The accompanying colored photographs illustrate the overall appearance of the new *Scaevola,* showing the colors as true as it is reasonably possible to obtain in colored reproductions of this type. Colors in the photographs may differ slightly from the color values cited in the detailed botanical description which accurately describe the colors of the new *Scaevola.*

The photograph at the top of the sheet comprises a side perspective view of a typical flowering plant of 'Bonscalib' grown in a container.

The photograph at the bottom of the sheet is a close-up view of typical flowers and leaves of 'Bonscalib'.

DETAILED BOTANICAL DESCRIPTION

The aforementioned photographs and following observations, measurements and values describe plants grown in Higashiomi, Shiga, Japan in containers in an outdoor nursery during the summer and under conditions which closely approximate commercial production. During the production of the plants, day temperatures averaged 23° C. and night temperatures averaged 13° C. Plants were about five months old when the photographs and the description were taken. In the description, color references are made to The Royal Horticultural Society Colour Chart, 2001 Edition, except where general terms of ordinary dictionary significance are used.

Botanical classification: *Scaevola aemula* cultivar Bonscalib.

Parentage:

*Female, or seed, parent.*—Proprietary selection of *Scaevola aemula* identified as code number 00-38.1, not patented.

*Male or pollen parent.*—Unknown proprietary selection of *Scaevola aemula,* not patented.

Propagation:

*Type.*—By vegetative cuttings.

*Time to initiate roots.*—About ten days at 20° C. to 25° C.

*Time to develop roots.*—About four weeks at 20° C. to 25° C.

*Root description.*—Fine, fibrous; light brown in color.

*Rooting habit.*—Freely branching.

Plant description:

*Plant form and growth habit.*—Compact, mounded and semi-trailing plant habit. Vigorous growth habit.

*Branching habit.*—Freely branching, lateral branches potentially forming at every node.

*Plant height.*—About 10.9 cm.

*Plant diameter* (*area of spread*).—About 42.4 cm.

Lateral branch description:

*Length.*—About 24.4 cm.

*Diameter.*—About 3.3 mm.

*Internode length.*—About 2.2 cm.

*Texture.*—Pubescent.

*Color.*—Close to 145A overlain with N199B.

Foliage description:

*Arrangement.*—Alternate, simple; sessile.

*Length.*—About 4.1 cm.

*Width.*—About 1.8 cm.

*Shape.*—Obovate to narrowly spatulate.

*Apex.*—Acute.

*Base.*—Obtuse to cuneate.

*Margin.*—Serrate.

*Texture, upper and lower surfaces.*—Pubescent; slightly coarse.

*Venation pattern.*—Pinnate, reticulate.

*Color.*—Developing foliage, upper surface: Close to 137C. Developing foliage, lower surface: Close to 138B. Fully expanded foliage, upper surface: Close to 137B; venation, 145A. Fully expanded foliage, lower surface: Close to 138B; venation, 145A.

Flower description:

*Flower type and shape.*—Zygomorphic, semi-circular, fan-shaped flowers with five petals fused at the base to form a tubular flower throat. Flower throat open along the upper surface exposing reproductive organs. Flowers not fragrant.

*Flower arrangement and quantity.*—Solitary sessile flowers arise from leaf axils. Flowers face mostly outwardly. Freely flowering habit, typically about nine flowers per lateral branch.

*Flowering time.*—Plants begin flowering after about four weeks and flower continuously from spring to late autumn in Australia. Flowers typically last about a week on the plant. Flowers persistent.

*Flower buds.*—Shape: Elongated ovate. Length: About 1.5 cm. Diameter: About 2.7 mm. Color: Close to N77C.

*Flowers.*—Diameter: About 1.7 cm by 3 cm. Depth: About 2.2 cm. Tube length: About 1.1 cm. Tube diameter: About 3.5 mm.

*Petals.*—Quantity: Five, fused at base. Shape: Lanceolate. Apex: Cuspidate. Margin: Entire. Length, above tube: About 1.4 cm. Width, above tube: About 5 mm. Texture, upper and lower surfaces: Smooth, glabrous. Color: When opening and fully opened, upper surface: Close to 84A; towards the base, 154D. When opening and fully opened, lower surface: Close to N87D; longitudinal central stripe, 155C. Throat: Close to 154C; venation, close to 187A. Tube: Close to 154C; venation, close to 187A.

*Sepals.*—Quantity: Two per flower. Length: About 7 mm. Width: About 1.1 mm. Shape: Lanceolate. Apex: Acute. Base: Obtuse. Margin: Entire. Texture, upper and lower surfaces: Slightly pubescent. Color, upper and lower surfaces: 137C.

*Reproductive organs.*—Androecium: Stamen quantity per flower: About five. Anther shape: Ellipsoidal. Anther size: About 2.4 mm by 1.2 mm. Anther color: Close to 174B. Pollen: Scarce. Gynoecium: Pistil quantity per flower: One. Pistil length: About 1.4 cm. Style color: Close to 157A. Stigma shape: Oblong. Stigma color: Close to 155D. Ovary color: Close to 144A.

*Seeds/fruits.*—Seed and fruit development have not been observed.

Garden performance: Plants of the new *Scaevola* have been observed to have good garden performance and to tolerate rain, wind and temperatures ranging from about 5° C. to about 35° C.

Pathogen/pest resistance: Plants of the new *Scaevola* have not been shown to be resistant to pathogens and pests common to *Scaevola.*

It is claimed:

1. A new and distinct *Scaevola* plant named 'Bonscalib' as illustrated and described.

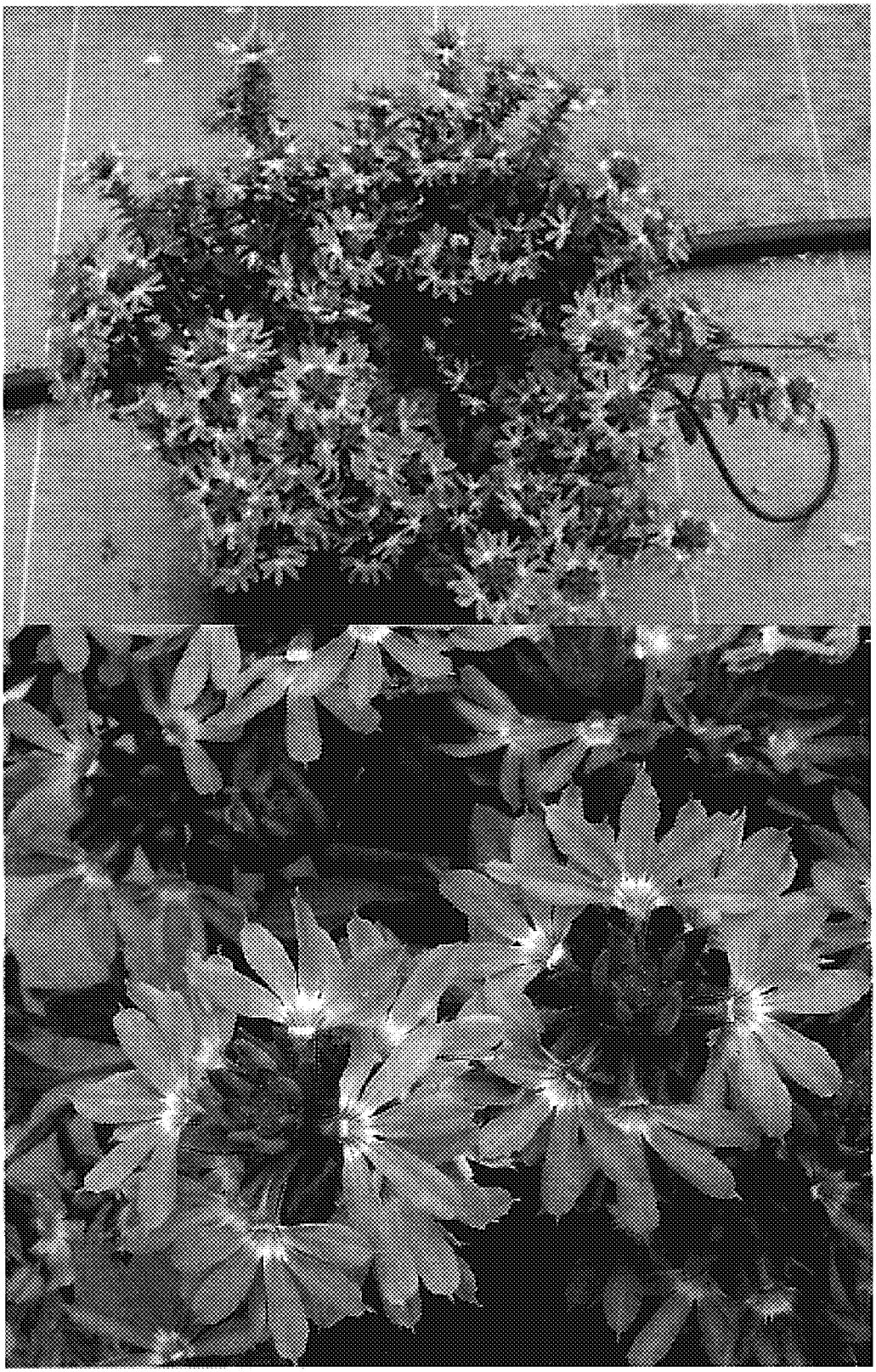

* * * * *